United States Patent
Bao et al.

(10) Patent No.: US 12,400,751 B2
(45) Date of Patent: Aug. 26, 2025

(54) METHODS AND SYSTEMS FOR RECURSIVE MEDICAL IMAGE DISPLAY PROTOCOLS

(71) Applicant: GE Precision Healthcare LLC, Wauwatosa, WI (US)

(72) Inventors: Yongjian Bao, Chicago, IL (US); Michael J Mercado, Chicago, IL (US); Mukesh Jain, Chicago, IL (US); Sayooj Cyriac, Chicago, IL (US); Hariom Kuntal, Chicago, IL (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 317 days.

(21) Appl. No.: 18/158,407

(22) Filed: Jan. 23, 2023

(65) Prior Publication Data

US 2024/0249822 A1    Jul. 25, 2024

(51) Int. Cl.
*G06T 11/00* (2006.01)
*A61B 6/46* (2024.01)
*G16H 30/20* (2018.01)
*G16H 50/70* (2018.01)

(52) U.S. Cl.
CPC ............. *G16H 30/20* (2018.01); *A61B 6/465* (2013.01); *G06T 11/00* (2013.01); *G16H 50/70* (2018.01)

(58) Field of Classification Search
None
See application file for complete search history.

(56) References Cited

U.S. PATENT DOCUMENTS

| | | | |
|---|---|---|---|
| 7,525,554 B2 | 4/2009 | Morita et al. | |
| 8,526,693 B2 | 9/2013 | Vijaykalyan et al. | |
| 9,152,760 B2 | 10/2015 | Sherman et al. | |
| 9,524,577 B1 | 12/2016 | Westerhoff et al. | |
| 9,933,930 B2 | 4/2018 | Gross et al. | |
| 10,169,534 B2 | 1/2019 | Day et al. | |
| 2005/0227154 A1* | 10/2005 | Motoki | A61B 6/4283 430/22 |
| 2013/0129165 A1 | 5/2013 | Dekel et al. | |
| 2019/0258396 A1* | 8/2019 | Barrick | G06F 3/0484 |

* cited by examiner

*Primary Examiner* — Yanna Wu
(74) *Attorney, Agent, or Firm* — McCoy Russell LLP

(57) ABSTRACT

A display protocol model having a recursive modular structure enables methods for displaying medical images. A method includes recursively generating a viewing layout which divides a display area of a display device into a plurality of medical image viewport placeholders by invoking a first layout having a first plurality of display area placeholders, where at least a first display area placeholder of the first layout is a first viewport placeholder including a first medical image characteristic parameter for at least one medical image, and at least a second display area placeholder, different from the first display area placeholder, includes an identifier of a second layout having a second plurality of display area placeholders positioned therein.

18 Claims, 11 Drawing Sheets

METHODS AND SYSTEMS FOR RECURSIVE MEDICAL IMAGE DISPLAY PROTOCOLS

FIELD

Embodiments of the subject matter disclosed herein relate to medical image display, and more particularly, to recursive medical image display protocols.

BACKGROUND

Display protocols are widely applied tools for displaying medical images. Typically, display protocols apply rules, which are defined manually and/or learned through artificial intelligence (AI), to multiple image groups of one or more imaging studies to allocate images of the multiple image groups into viewport placeholders of a display. Structure among the viewport placeholders is less understood than allocation results. For example, conventional methods for positioning viewport placeholders in a display area may include dragging and dropping viewport placeholders in the display area, or labeling regions of the display area as different viewport placeholders. This may not include defining positions of each viewport within a layout, or defining a layout as a given arrangement of viewport placeholders. Instead, generating a layout which includes a plurality of viewport placeholders, which may be the same or different sizes and shapes, may be a manual process. Additionally, adding or rearranging viewport placeholders in an existing layout may include generating a new layout, instead of modifying the existing layout. Layouts may be user and/or institution specific, due to the manual nature of layout generation. Thus, it may be challenging to share display protocols and resulting layouts among users and/or institutions, and it may be additionally challenging to generate new layouts from existing display protocols.

BRIEF DESCRIPTION

In one embodiment, a method for displaying multiple images based on multiple modular display protocols comprises receiving, via a graphical user interface (GUI) displayed on a display device, a first user request to view one or more medical images from a set of medical images using a first medical image display protocol, in response to the first user request, retrieving the first medical image display protocol from a display protocol library stored on a memory, the first medical image display protocol including a first layout having a plurality of display area placeholders, wherein each display area placeholder of the plurality of display area placeholders either defines a viewport placeholder having a respective medical image medical image characteristic parameter that defines a characteristic of at least one medical image to be displayed in that viewport placeholder, or references a display protocol stored in the display protocol library, invoking, via a processor, the first medical image display protocol to divide a display area of the display device into the plurality of display area placeholders, determining that a first display area placeholder of the plurality of display area placeholders references a second medical image display protocol, and in response, retrieving the second medical image display protocol from the display protocol library, the second medical image display protocol including a second layout having one or more additional display area placeholders, invoking, via the processor, the second medical image display protocol to divide the first display area placeholder into the one or more additional display area placeholders, and populating each display area placeholder which defines a viewport placeholder with a corresponding medical image from the one or more medical images based on the medical image medical image characteristic parameter for each viewport placeholder and the characteristic of each medical image.

In this way, medial image display protocols may be modularly constructed and have a recursive nature, enabling an infinite number of unique display layouts may be generated from a finite number of medical image display protocols. A medical image display protocol generated using the methods described herein may include references to other display protocols in at least one display area placeholder, instead of explicitly containing instructions for that display protocol, or being defined as multiple viewport placeholders.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

The following description relates to various embodiments for a display protocol model having a recursive modular structure. A first medical image display protocol may include at least one display area placeholder which refers to a second medical image display protocol, such that when the first medical image display protocol is invoked, the second medical image display protocol is inherently invoked. In some examples, additional display area placeholders of the at least one display area placeholder of the first medical image display protocol may refer to additional medical image display protocols. Additionally, in some examples, the second medical image display protocol may include at least one display area placeholder which refers to additional medical image display protocols. The recursive structure of the first medical image display protocol enables multiple medical image display protocols to be executed by invoking the first medical image display protocol.

Figure 1:
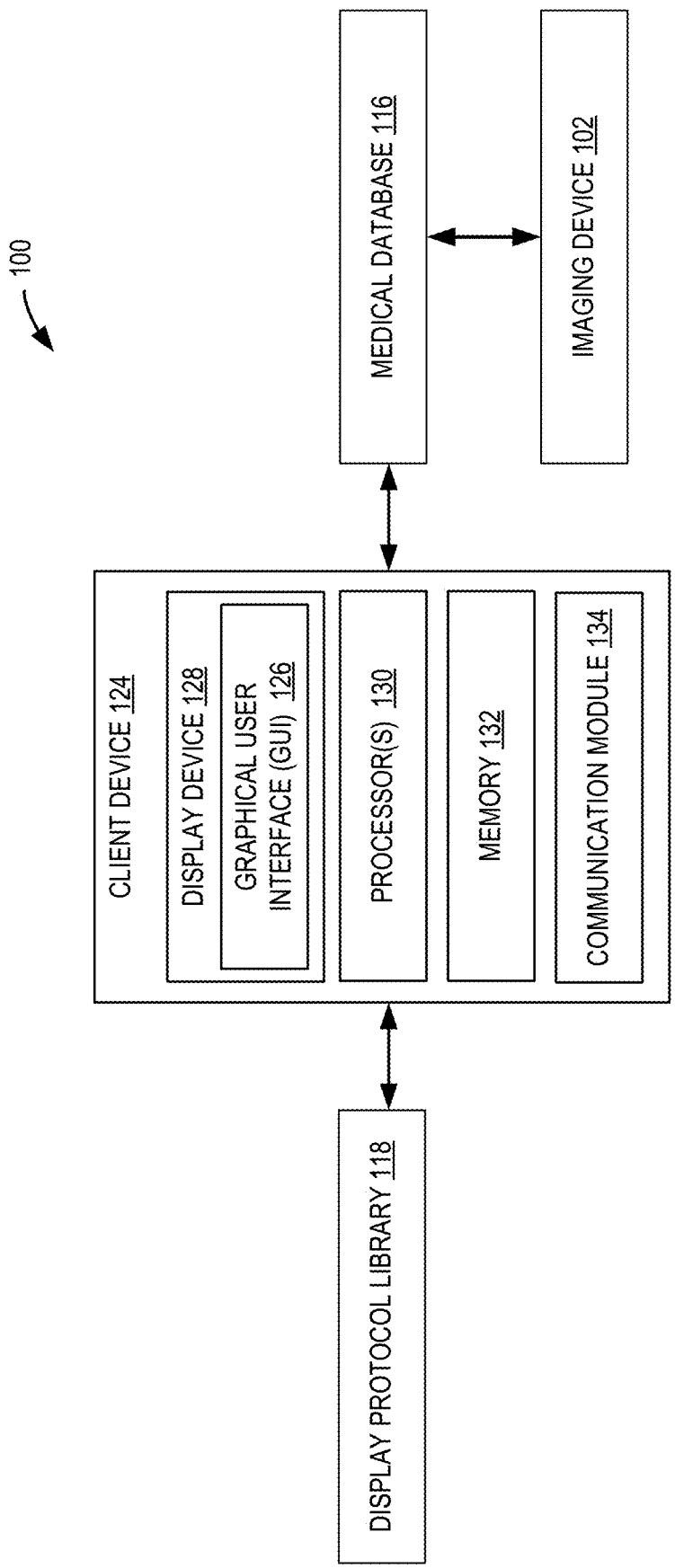
FIG. 1 shows a schematic block diagram of an example system for medical data transmission.
Figure 2:
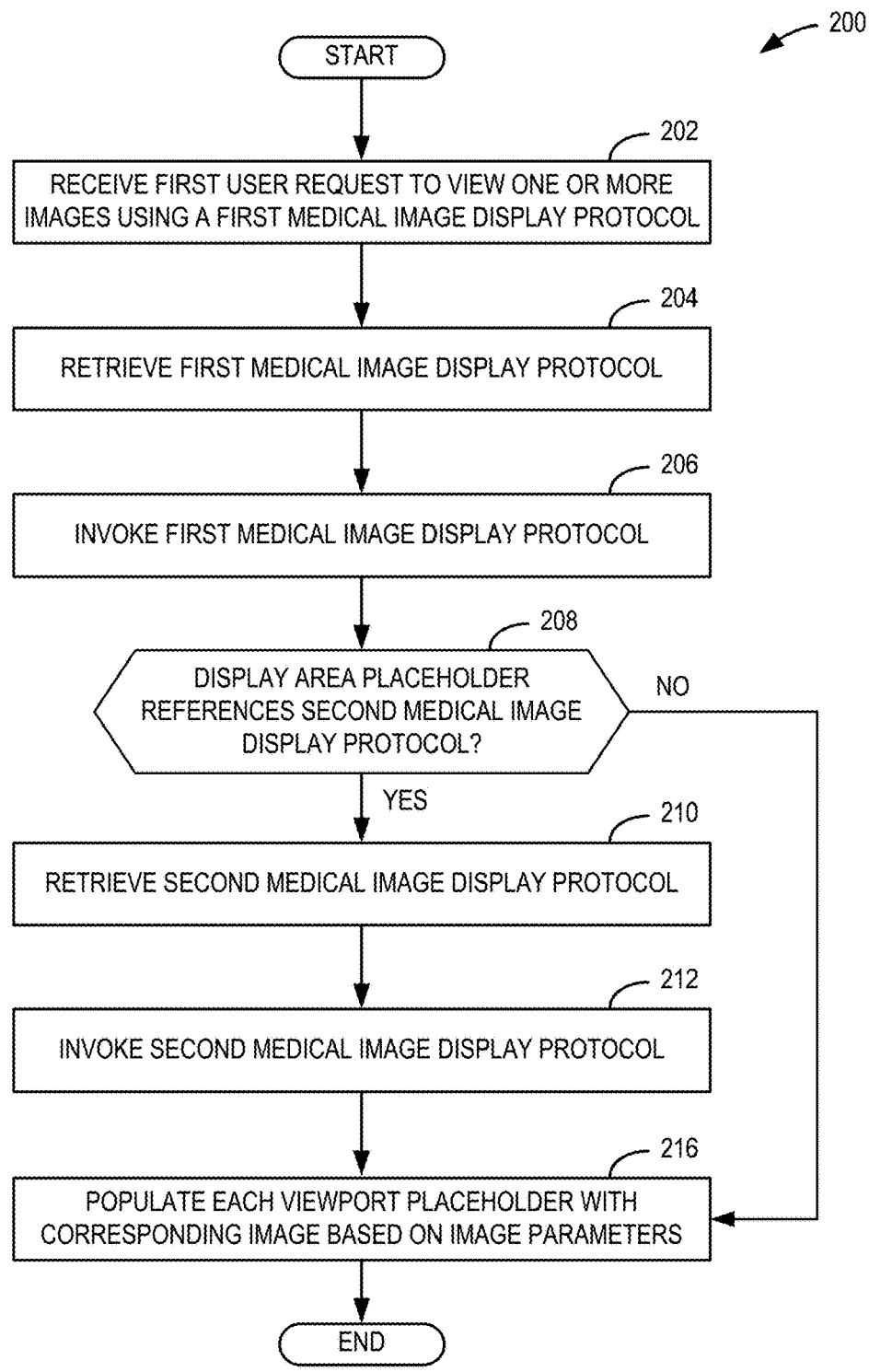
FIG. 2 is a flow chart illustrating an example high-level method for displaying medical images according to a recursive medical image display protocol.
Figure 6:
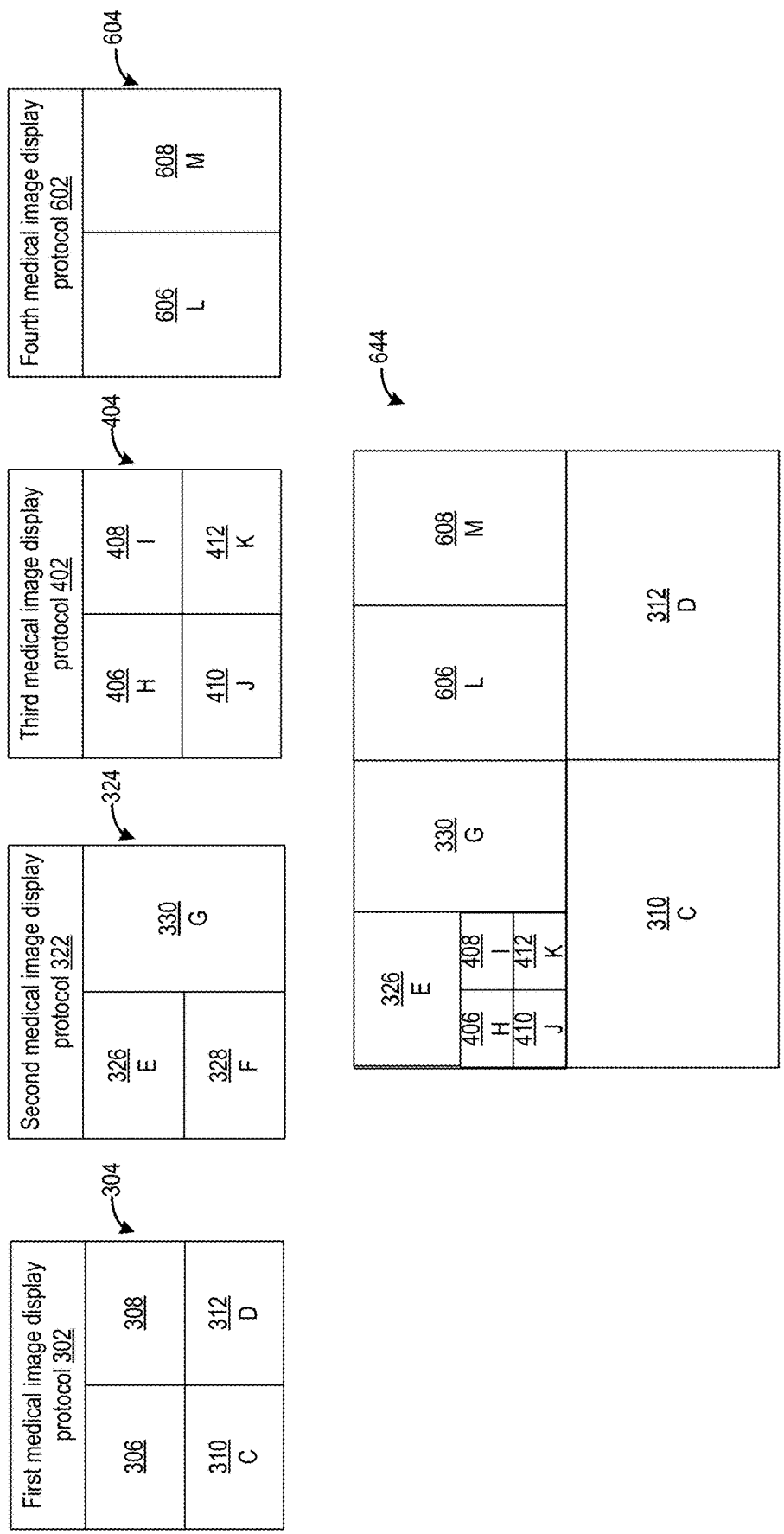
FIG. 6 shows a graphical representation of a first medical image display protocol which references a second medical image display protocol, a third medical image display protocol, and a fourth medical image display protocol.
Figure 7:
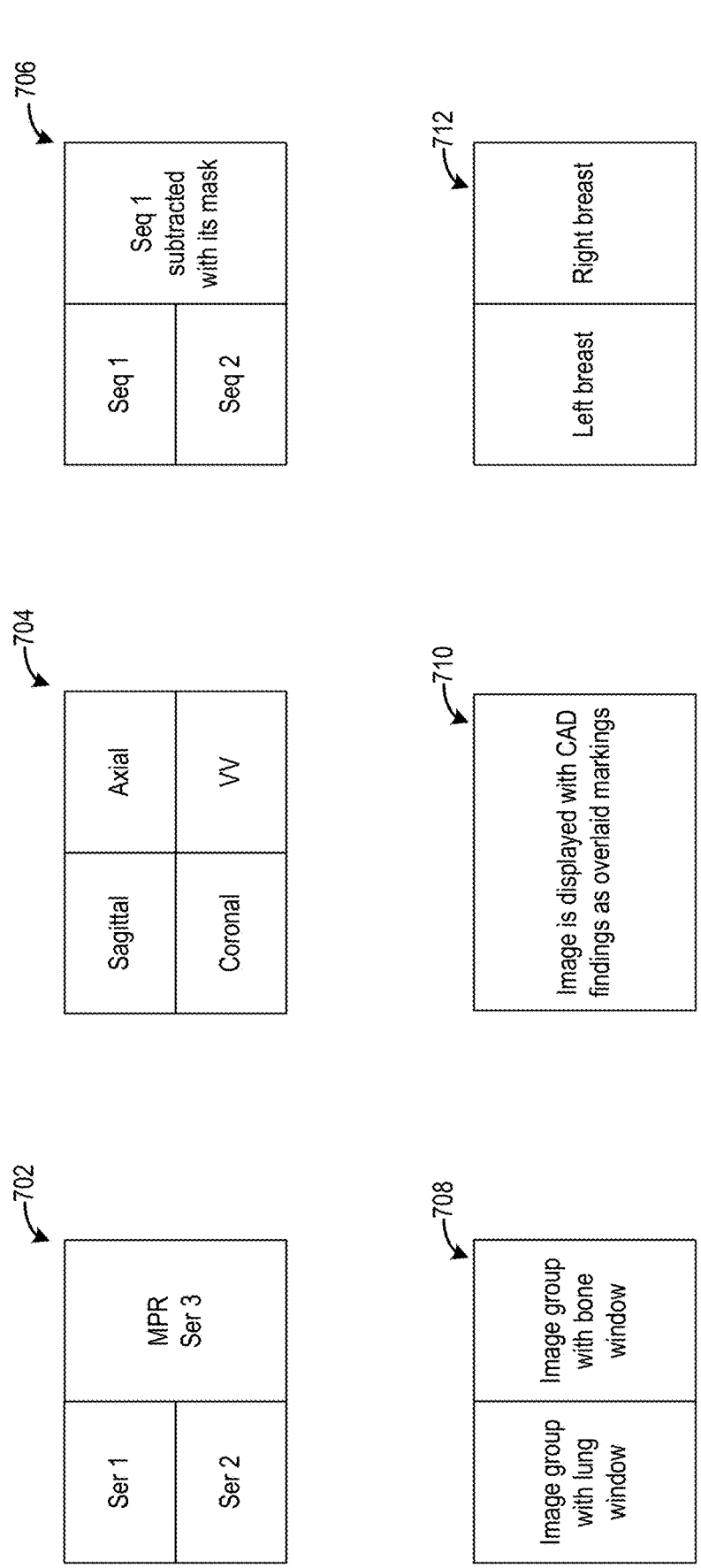
FIG. 7 shows a plurality of layouts defined by medical image display protocols.
Figure 8:
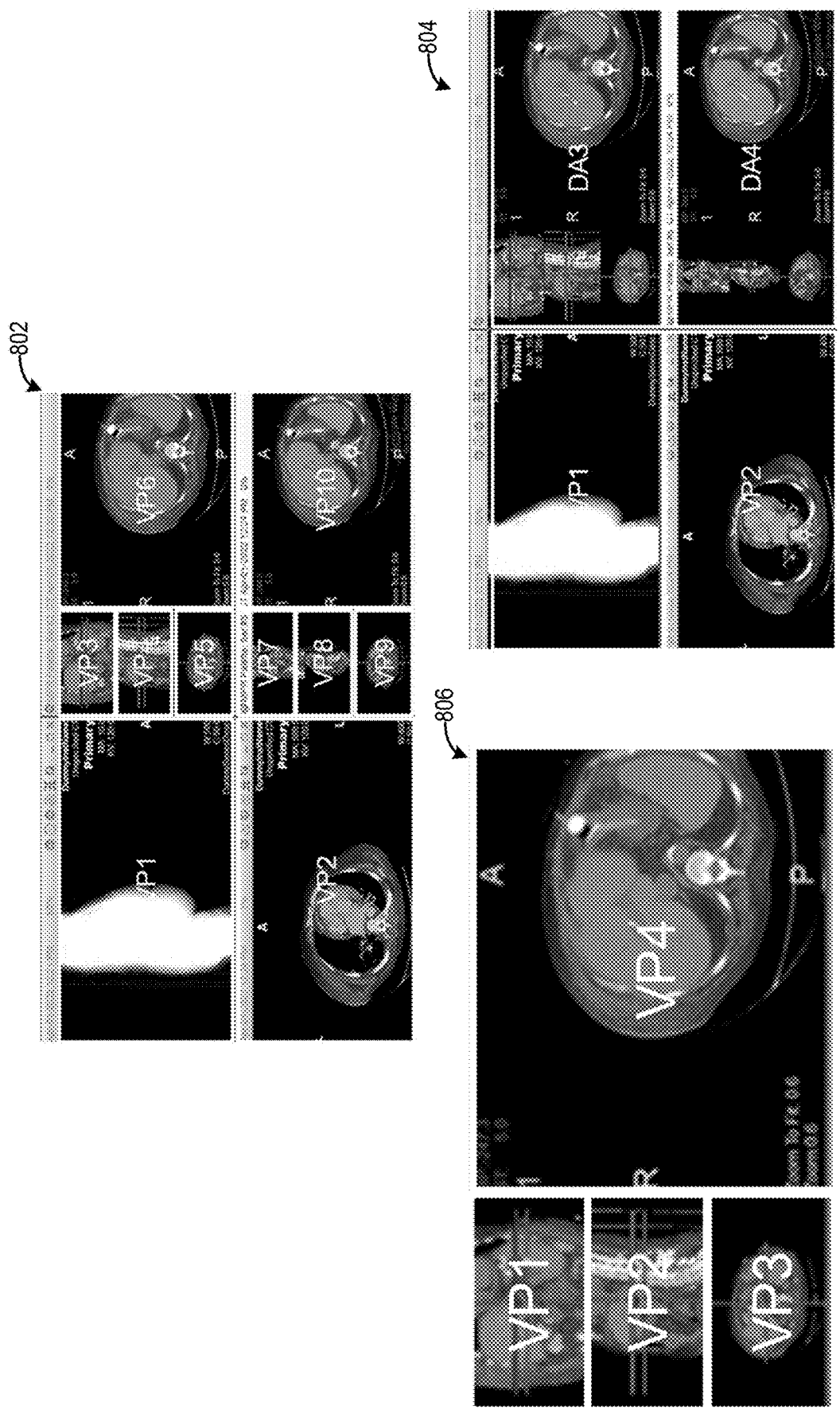
FIG. 8 shows example displays generated using a conventional display protocol and using a recursive medical image display protocol described herein.
Figure 9:
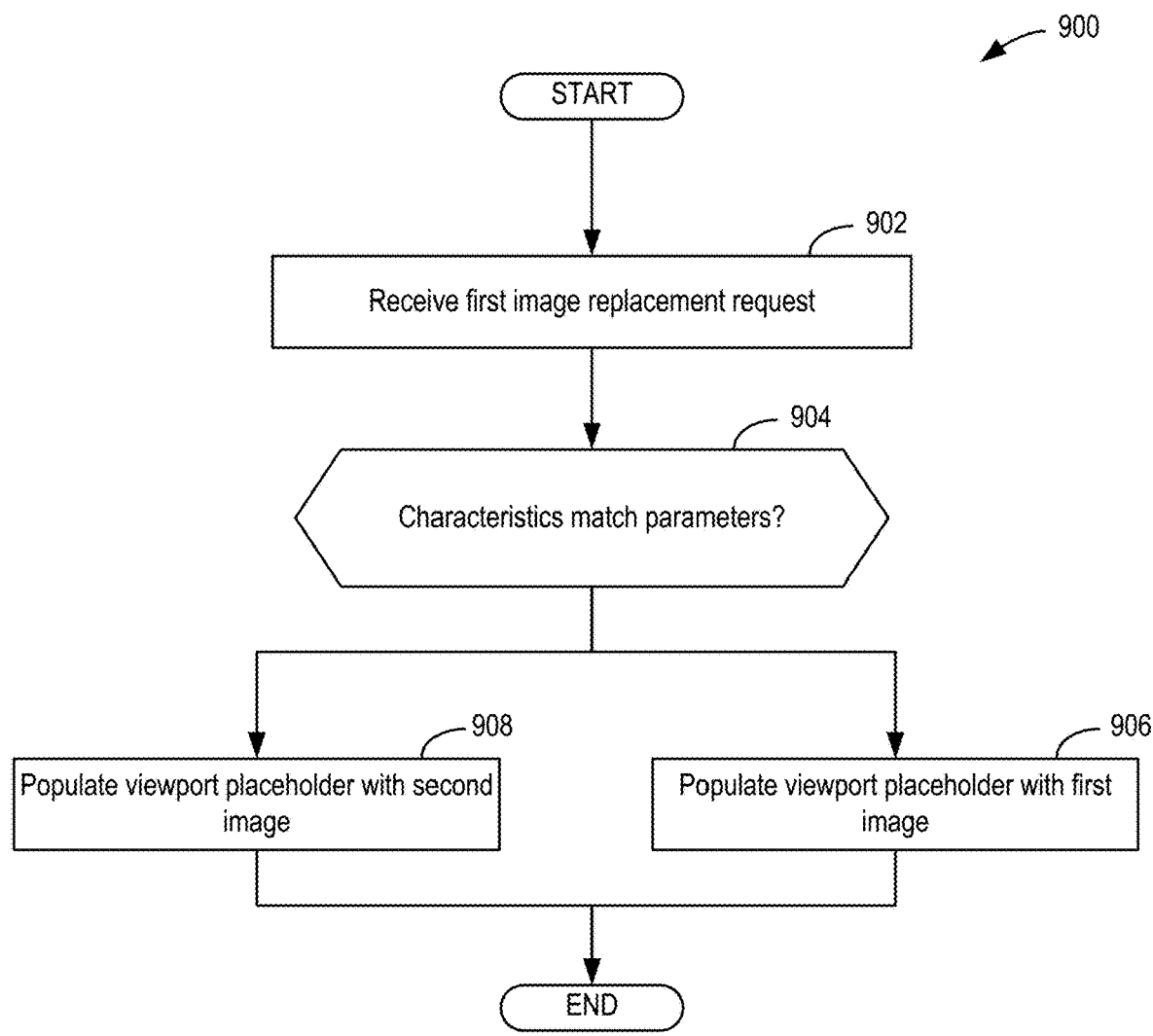
FIG. 9 is a flow chart illustrating an example method for replacing at least a first image positioned in a viewport placeholder with a second image.
Figure 10:
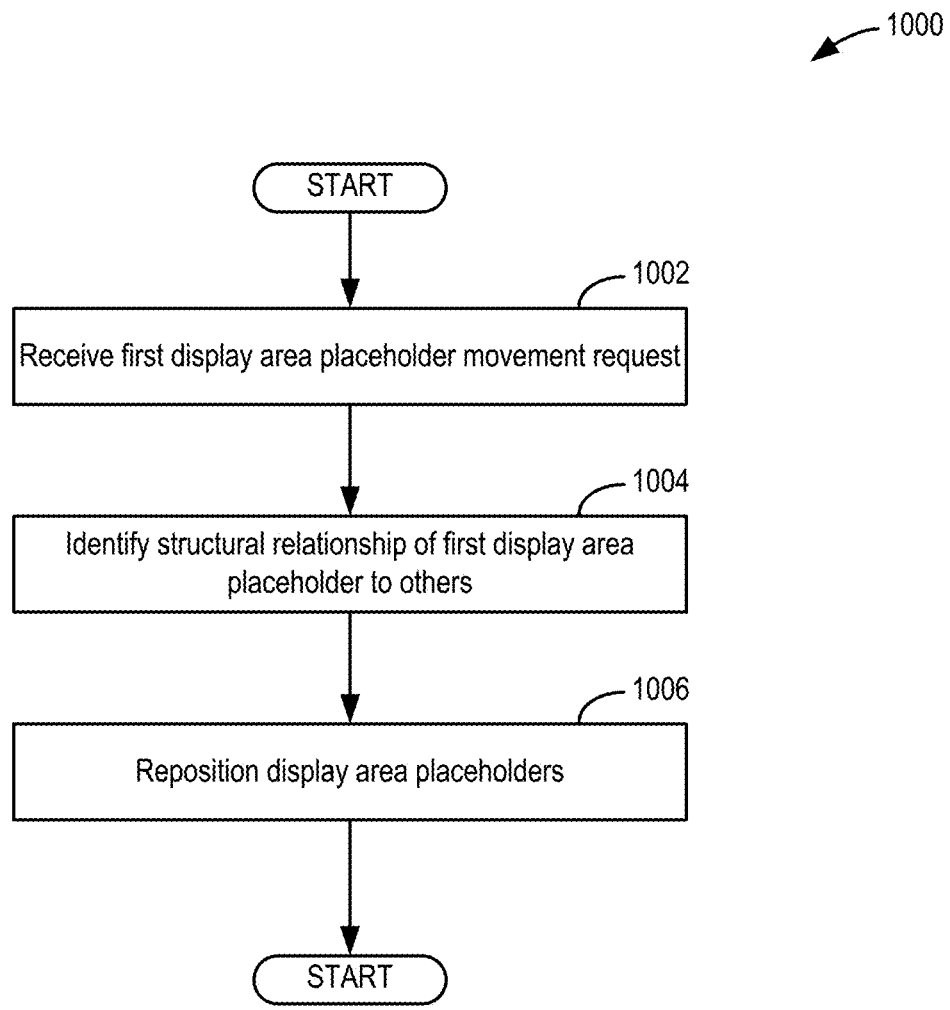
FIG. 10 is a flow chart illustrating an example method for repositioning at least one display area placeholder in response to receiving a request.
Figure 11:
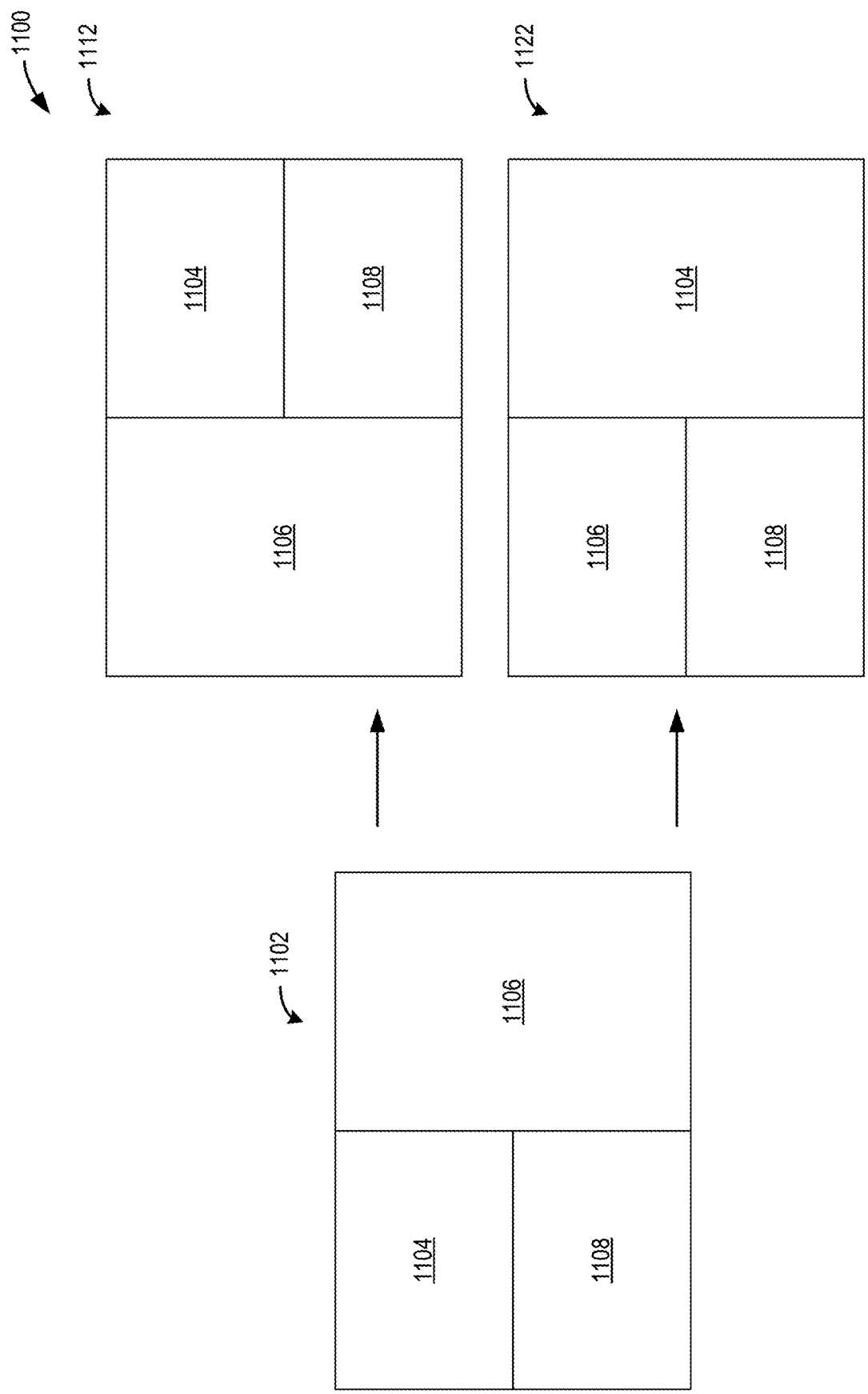
FIG. 11 shows a graphical representation of a display area, including display area placeholders, before and after repositioning of at least one display area placeholder, as described with respect to FIG. 10.

The methods described herein for generating and executing display area protocols may be performed by a client device which is communicably coupled to databases storing display area protocols and medical images, as shown schematically in FIG. 1. A flow chart illustrating an example high-level method for displaying medical images according to a recursive medical image display protocol is shown in FIG. 2. The recursive medical image display protocol may be used to generate a plurality of viewing layouts which are displayed on a display area of a display device. Example viewing layouts are described with respect to FIGS. 3-6. The recursive medical image display protocol, herein referred to as the first medical image display protocol, refers to at least one medical image display protocol besides itself. Example medical image display protocols, some of which may be the first medical image display protocol, are shown in FIG. 7. Viewport placeholders of medical image display protocols are populated with corresponding medical images. A comparison of generating a display using a conventional display protocol and using the recursive medical image display protocol described herein is described with respect to FIG. 8. Following generation of the display, modifications may be made to the display in response to received requests. For example, FIG. 9 is a flow chart illustrating an example method for replacing at least a first image positioned in a viewport placeholder with a second image, and FIG. 10 is a flow chart illustrating an example method for repositioning at least one display area placeholder in response to receiving a request. An example graphical representation of a display area, including display area placeholders, before and after repositioning of at least one display area placeholder, as described with respect to FIG. 10, is shown in FIG. 11.

The medical image display protocol described herein is a recursive model, where display protocols (e.g., from a display protocol library) are recursively specified and are used as building blocks to define the first medical image display protocol. The display protocols from the library include fundamental, common-purpose display protocols which may be frequency implemented, for example, by different users and/or for different imaging studies. Recursively building the display protocol model adds structural information which can be understood by application software. For example, traditional display protocols may directly define a collection of viewport placeholders in at least one display and provide less information about the relationship among the collection of viewport placeholders. Recursively building the display protocol model may include more information about relationships between viewport placeholders compared to traditional display protocols, such as why two viewport placeholders may be positioned side by side in the display. In this way, a display protocol model which is recursively defined may recursively specify display protocols at an image group level and a single DICOM instance, for example, in addition to an exam/imaging study level. In some examples, a class code may be applied to the display protocol model to indicate an application scope of recursion. Additionally, the display protocol model, as well as display protocols included therein, may specify a display area size and location within a display, which may be less than a total size of the display. Additional metadata may be included in the display protocol model to describe an application intention thereof.

FIG. 1 shows a block diagram illustrating a system 100 for medical data transmission and display. The system 100 may be used to transmit medical data, specifically medical images and associated data/metadata, collected by a hospital modality and stored in a medical database to a client device for display. Additionally, the system 100 may be used to transmit medical image display protocols stored in a display protocol library to the client device to be invoked for generating a display which includes the medical images. The medical image display protocols may be recursive, such that invoking a first medical image display protocol inherently invokes at least one additional medical image display protocol which is referenced by the first medical image display protocol. Each medical image display protocol further includes information about structural relationships among display area placeholders of the respective medical image display protocols and medical image display protocols referenced therein. In this way, displays of medical images may be generated automatically which include a plurality of medical images which are related to each other in image type, image subject, view of interest, and so on, as further described herein.

An imaging device 102 may be a hospital modality, such as a computed tomography (CT) system, an x-ray angiography (XA) system, a position emission tomography (PET) system, a radio fluoroscopy (RF) system, and a nuclear medicine (NM) system. The imaging device 102 may perform imaging procedures, such as radiation observations in which a patient is exposed to a radiation dose. The imaging device 102 may share data collected by a respective modality to a storage device according to one or more standards (e.g., Digital Imaging and Communications in Medicine (DICOM®), Health Level Seven (HL7®), ANSI X12N, etc.). The imaging device 102 may be operably coupled to a medical database 116 via a wired connection, a wireless connection, and/or any method for communicably connecting systems. As described herein "operably coupled" is to be understood as coupling of elements via connectivity methods (e.g., wired connection, wireless connection, and so on) which enable transfer of data, signals, requests, and/or other information among the operably coupled elements.

The medical database 116 is configured to receive medical images from at least one imaging device 102 and store the medical images, as well as associated data and/or metadata. The medical database 116 may be an external database or a local database (e.g., housed on a device of the system 100). The medical database 116 may be a database stored in a mass storage device configured to communicate with secure channels (e.g., HTTPS and TLS), and store data in encrypted form. For example, the medical database 116 may be communicably coupled to, and therefore able to exchange data with, a plurality of medical providers, such as client devices at the same or different hospitals, provider offices, field offices, and so on.

A display protocol library 118 may be configured to receive and store medical image display protocols. Each of a plurality of medical image display protocols stored in the display protocol library 118 may define a layout of a plurality of display area placeholders and a structural relationship among the plurality of display area placeholders. A display area placeholder may either define a viewport placeholder or reference another medical image display protocol stored in the display protocol library. The viewport placeholder indicates a group of medical images to be displayed therein, where the group may include at least one medical image. The viewport placeholder includes a medical image characteristic parameter of the group of medical images, which indicates a characteristic of the at least one medical image to be positioned therein. As further described herein, a medical image with characteristics which correspond with the medical image characteristic parameter of the group of medical images of a viewport placeholder may be automatically positioned in the viewport placeholder for display. The characteristic may be a type of imaging method used to capture the image (e.g., X-ray, ultrasound, MRI, CT, and so on), an anatomy shown in the image, an image plane (e.g., sagittal, axial, coronal), a type of marking overlaid on the medical image, an alignment of the medical image, and so on. In some examples, some medical image display protocols stored in the display protocol library 118 may include the same and/or different viewport placeholders and references to medical image display protocols as each other. Additionally, some medical image display protocols may have the same or a different number, as well as the same or a different arrangement of display area placeholders, including the same or a different number, as well as the same or a different arrangement of viewport placeholders. Some examples of display area placeholders are described in greater detail in FIG. 7.

The display protocol library 118 may store medical image display protocols which are commonly used, for example, by different users, for different imaging studies, and so on. For example, the display protocol library 118 may include three dimensional (3D) image stack, multiplanar reconstruction (MPR)/maximum intensity projection (MIP), subtract, anatomic laterality, temporal image sequence, sequence of living and mask images, and bi-laterality image pair, as well as user-generated medical image display protocols. The plurality of medical image display protocols may be comprised of medical image display protocols which are defined manually and/or learned through artificial intelligence or machine learning. For example, a user may create and define a medical image display protocol using the display protocol library 118, where a first display protocol is recursively built to include a second display protocol. In other examples, a medical image display protocol may be automatically generated based on user actions using AI, such as generating a layout of a plurality of display area placeholders based on a frequency of positioning of viewport placeholders with respect to other viewport placeholders.

By storing a plurality of medical image display protocols in the display protocol library 118, medical image display protocols which use recursively include medical image display protocols may be quickly and easily constructed and executed by a user and/or a processor, for example. Structural relationships among the display area placeholders of a medical image display protocol may be understood and applied by software to enable further automated capabilities in medical image interpretation workflows. Methods for recursive medical image display protocols, as described herein, may be applied to aspects of traditional display protocols, including creation and editing, learning, application, and maintenance in interpretation workflows.

Medical image display protocol models may be shared among users, such as across health institutions and/or imaging disciplines. The display protocol library 118 may be accessed by multiple different users, and may be accessed remotely. For example, the display protocol library 118 may be stored on a server which is communicably coupled to at least one workstation of at least one location (e.g., medical office) through a wired and/or wireless connection. In this way, commonly used elements of a medical image display protocol (e.g., the medical image display protocols stored on the display protocol library 118) may be shared among users. Within the display protocol library 118, each medical image display protocol may be categorized and/or labeled to indicate uses for the given medical image display protocol, such that users who are less experienced in medical image display protocol construction may be able to quickly construct medical display protocol which recursively include more than one medical image display protocol.

For example, medical image display protocols stored in the display protocol library 118 and medical images stored in the medical database 116 may be accessed by a client device 124. The client device 124 may include a processor 130, a memory 132, a communication module 134, a graphical user interface (GUI) 126, a display device 128 (e.g., screen or monitor), and/or other subsystems, and may be in the form of a desktop computing device, a laptop computing device, a tablet, a smart phone, or other device. The client device 124 may be located locally at a hospital (e.g., as part of hospital administration) and/or remotely from the hospital (such as a user's mobile device). The display protocol library 118 and the medical database 116 may each be operably coupled to the client device 124 via a wired interface (e.g., a data bus, a Universal Serial Bus (USB) connection, etc.) and/or a wireless interface (e.g., radio frequency, infrared, near field communication (NFC), etc.). For example, communication module 134 may communicate via wired local area network (LAN), wireless LAN, wide area network (WAN), etc. using any past, present, or future communication protocol (e.g., BLUETOOTH™, USB 2.0, USB 3.0, etc.). Memory 132 includes one or more data storage structures, such as optical memory devices, magnetic memory devices, or solid-state memory devices, for storing programs and routines executed by processor(s) 130 to carry out various functionalities disclosed herein. Memory 132 may include any desired type of volatile and/or non-volatile memory such as, for example, static random access memory (SRAM), dynamic random access memory (DRAM), flash memory, read-only memory (ROM), etc. Processor(s) 130 may be any suitable processor, processing unit, or microprocessor, for example. Processor(s) 130 may be a multi-processor system, and, thus, may include one or more additional processors that are identical or similar to each other and that are communicatively coupled via an interconnection bus.

As further described with respect to FIG. 2, in response to the processor 130 receiving a user request via the GUI 126, a first medical image display protocol may be retrieved from the display protocol library 118 by using the processor 130 to execute instructions stored on the memory 132 of the client device 124. The first medical image display protocol may reference a second medical image display protocol, and the processor 130 may recursively retrieve the second medical image display protocol from the display protocol library 118. In executing the instructions stored on the memory 132, the processor 130 may recursively generate a display, to be displayed on a display device 128, which divides a display area of the display device 128 into a first layout having a first plurality of display area placeholders (e.g., as defined by the first medical image display protocol), where at least a first display area placeholder of the first layout has a medical image positioned therein, and at least a second display area placeholder, different from the first display area placeholder, has a second layout with a second plurality of display area placeholders (e.g., as defined by the first medical image display protocol), positioned therein, where at least a third display area placeholder of the second layout has a medical image positioned therein. In this way, a plurality of medical images may be displayed in the display area, where the display includes positioning of the plurality of medical images as defined by the medical image display protocols. Further detail regarding structural relationships of the medical image display protocols is described herein.

As used herein, the terms "sensor," "system," "unit," or "module" may include a hardware and/or software system that operates to perform one or more functions. For example, a sensor, module, unit, or system may include a computer processor, controller, or other logic-based device that performs operations based on instructions stored on a tangible and non-transitory computer readable storage medium, such as a computer memory. Alternatively, a sensor, module, unit, or system may include a hard-wired device that performs operations based on hard-wired logic of the device. Various modules or units shown in the attached figures may represent the hardware that operates based on software or hard-wired instructions, the software that directs hardware to perform the operations, or a combination thereof.

"Systems," "units," "sensors," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

Figure 3:
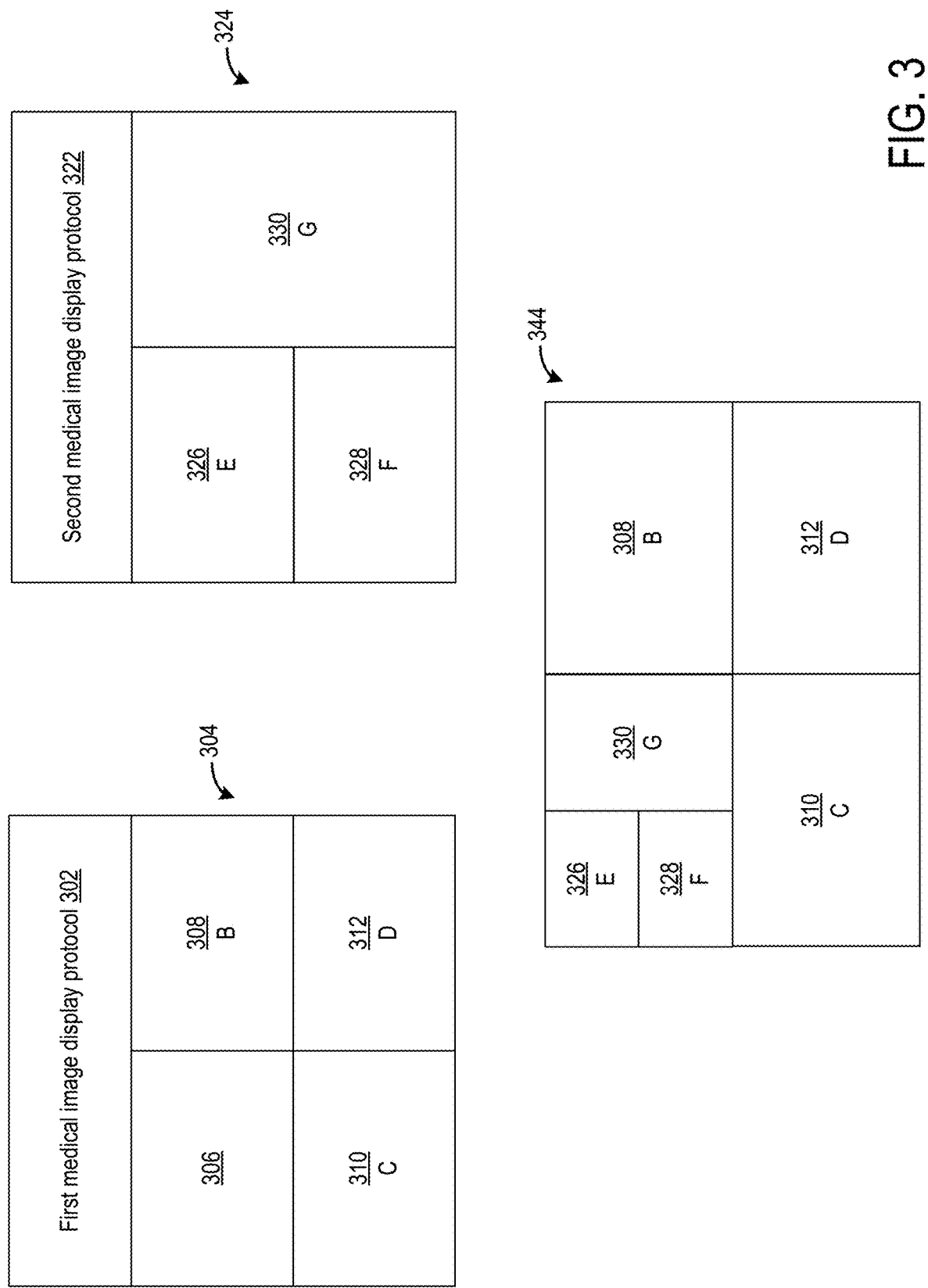
FIG. 3 shows a graphical representation of a first medical image display protocol which references a second medical image display protocol.

FIG. 2 illustrates a method 200 for displaying medical images according to a medical image display protocol. The method 200 may be carried out according to non-transitory instructions stored in the memory 132 of the client device 124 of FIG. 1. Briefly, the client device 124 receives a user request to view one or more medical images using a first medical image display protocol, which defines a first layout in which the medical images are to be arranged. The first layout includes a reference to a second medical image display protocol, which defines a second layout in which additional medical images are to be arranged. The method 200 includes invoking both the first medical image display protocol and the second medical image display protocol, and populating each viewport placeholder of each medical image display placeholder with a corresponding medical image. Examples of medical image display protocol layouts and a display used by and generated according to the method 200 are shown in FIG. 3.

At 202, the method 200 includes receiving a first user request to view one or more images using a first medical image display protocol. The first user request may be received via a GUI displayed on a display device (e.g., the GUI 126 of the display device 128 of FIG. 1). Medical images may be stored on a database of a server or other storage device which is communicably coupled to the client device 124, such as the medical database 116 of FIG. 1. The first user request includes a selection of one or more medical images from the database. Selected medical images may include medical images captured of a single patient, and/or medical images captured in a given time period, medical images captured using a single imaging device or type of imaging device, medical images captured by a single healthcare provider, all of which may be for a single patient or for more than one patient, for example. Selection of the one or more images indicated by the first user request, may indicate a plurality of medical images which the processor 130 may use to populated viewport placeholders of medical image display protocols, as further described herein. Described another way, implementing the first medical image display protocol includes displaying the selected images according to a layout of the first medical image display protocol.

The first medical image display protocol may be one of a plurality of medical image display protocols stored in the display protocol library 118. For example, the first user request may include selection of the first medical image display protocol based on medical image types which may be included in a resulting display. The first medical image display protocol may be manually selected in some examples and, in other examples, may be automatically selected based on the selected medical images. As further described herein, selection of the first medical image display protocol may inherently include selection of a second medical image display protocol when the first medical image display is recursively defined as including the second medical image display protocol.

At 204, in response to receiving the first user request, the method 200 includes retrieving the first medical image display protocol from the display protocol library 118. The first medical image display protocol includes instructions for a first layout having a plurality of display area placeholders, as further described herein. For example, the first layout may divide a display area into four equal sized quadrants, each of which is a display area placeholder. As briefly described above, each display area placeholder of the plurality of display area placeholders either defines a viewport placeholder having a respective medical image characteristic parameter of a group of medical images that defines a characteristic of at least one medical image to be displayed in that viewport placeholder, or references a display protocol stored in the display protocol library 118.

At 206, the method 200 includes invoking, via a processor (e.g., the processor 130 of FIG. 1), the first medical image display protocol to divide a display area of the display device (e.g., the display device 128) into the plurality of display area placeholders. For example, invoking the first medical image display protocol may include executing instructions to detect a size and shape of the display area. The display area may then be divided into the plurality of display area placeholders according to the layout of the first medical image display protocol. For example, the layout may include a first display area placeholder, a second display area placeholder, a third display area placeholder, and a fourth display area placeholder, as described in further detail in FIG. 3. Each of the plurality of display area placeholders may have an equal size and shape, in some examples. In other examples, the layout may have a different number of display area placeholders (e.g., greater than or less than four), where each of the plurality of display area placeholders may be the same size and shape and/or a different size and shape. As further described herein, a structural relationship of display area placeholders (e.g., in which display area placeholder another medical image display protocol is referenced) within the layout is defined by the display protocol.

At 208, the method 200 includes determining if a display area placeholder of the plurality of display area placeholders references a second medical image display protocol. When stored in a database, such as the display protocol library 118, each medical image display protocol has an associated identifier. A display area placeholder may reference a medical image display protocol by referencing the identifier of the desired medical image display protocol, rather than specifying a medical image characteristic parameter of a group of medical images. In some examples, more than one display area placeholder of the first medical image display protocol may reference additional medical image display protocols (e.g., different from the second medical image display protocol). Examples where the first layout of the first medical image display protocol references more than one medical image display protocol are described with respect to FIGS. 4-6. In the example described with respect to FIG. 2, it is to be understood that the first display area placeholder references the second medical image display protocol, and the second display area placeholder, third display area placeholder, and fourth display area placeholder each reference a different viewport placeholder. In examples where more than one of the plurality of display area placeholders of the first medical image display protocol references a medical image display protocol, each referenced medical image display protocol may be retrieved and invoked as described herein with reference to the second medical image display protocol. If a display area placeholder of the plurality of display area placeholders does not reference a second medical image display protocol, the method 200 proceeds to operation 216, as further described below.

In response to determining that the first display area placeholder references the second medical image display protocol, at 210, the method 200 includes retrieving the second medical image display protocol from the display protocol library 118. The second medical image display protocol includes instructions for a second layout having at least one display area placeholder (e.g., one or more additional display area placeholders, with respect to the plurality of display area placeholders of the first medical image display protocol). Similar to the plurality of display area placeholders of the first layout, each of the at least one display area placeholder of the second layout may define either a viewport placeholder or reference a display protocol.

At 212, the method 200 includes invoking, via the processor, the second medical image display protocol to divide the first display area placeholder of the first medical image display protocol into the second layout having at least one display area placeholder. For example, the second layout may include a fifth display area placeholder, a sixth display area placeholder, and a seventh display area placeholder. Each of the at least one display area placeholder of the second layout may have the same or a different size and shape. For example, the fifth display area placeholder and the sixth display area placeholder may be the same size and shape, and the seventh display area placeholder may be larger than the fifth display area placeholder and the sixth display area placeholder. In the example described herein with respect to the method 200, the fifth display area placeholder, the sixth display area placeholder, and the seventh display area placeholder each reference a different viewport placeholder. In other examples, at least one of the plurality of additional display area placeholders of the second medical image display protocol may reference a display protocol of the display protocol library 118. The second medical image display protocol may be any user-generated, AI-generated, or manufacturer-generated display protocol which is stored in display protocol library 118.

At 216, the method 200 includes populating each display area placeholder which defines a viewport placeholder with at least one medical image having a characteristic which corresponds with the medical image characteristic parameter of the group of medical images defined by the viewport placeholder. For example, at least one medical image (e.g., which is selected in the first user request) which has a characteristic corresponding to the medical image characteristic parameter of the group of medical images of a viewport placeholder is automatically sized and positioned to fit within the viewport placeholder. As briefly described above, each viewport placeholder defined by either the first medical image display protocol and the second medical image display protocol includes at least one respective medical image characteristic parameter of the group of medical images that defines a characteristic of at least one image to be displayed in that viewport placeholder. The medical image characteristic parameter may be a type of imaging method used to capture the image (e.g., X-ray, ultrasound, MRI, CT, and so on), an anatomy shown in the image, an image plane (e.g., sagittal, axial, coronal), a type of marking overlaid on the medical image, an alignment of the medical image, and so on. The set of medical images selected in the first user request may include a plurality of medical images, some or all of which may have characteristics which correspond to the medical image characteristic parameter of the group of medical images of the first layout and/or the second layout. For example, characteristics of a medical images may be stored in metadata of the medical image.

The method 200 may proceed with populating viewport placeholders with corresponding medical images until all viewport placeholders are populated with a corresponding image. For example, the second display area placeholder, the third display area placeholder, and the fourth display area placeholder of the first layout of the first medical image display protocol are each populated with an image having a characteristic which corresponds to a respective medical image characteristic parameter of the viewport placeholder referenced by the display area placeholder. The first display area placeholder of the first layout is populated with three medical images according to the second layout of the second medical image display protocol: each of the fifth display area placeholder, the sixth display area placeholder, and the seventh display area placeholder are populated with at least one image having a characteristic which corresponds to a respective medical image characteristic parameter of the viewport placeholder referenced by the second display area placeholder. Further detail regarding population of viewport placeholders with corresponding medical images is described with respect to FIGS. 3-6 and 8.

In this way, a display area (e.g., of the display device 128 of FIG. 1) is populated with a display which includes a plurality of medical images arranged according to the first medical image display protocol and the second medical image display protocol. The first medical image display protocol is recursively defined to include the second medical image display protocol, such that invoking the first medical image display protocol inherently includes invoking the second medical image display protocol. The display generated by populating display area placeholders defined by the first medical image display protocol thus includes medical images which correspond to the medical image characteristic parameters of viewport placeholders of both the first medical image display protocol and the second medical image display protocol.

The recursive nature of the systems and methods described herein, where at least one display area placeholder of a first medical image display protocol refers to an additional medical image display protocol, is used to define structural relationships of medical image displays. A structural relationship, including a positioning of each of the display area placeholders with respect to each other and within the display area, may be useful in analysis of displayed medical images. By referencing an additional medical image display protocol in a display area placeholder of a first medical image display protocol, the first medical image display protocol explicitly specifies that, in the display area placeholder, selected medical images will be organized and displayed as defined by the referenced additional medical image display protocol. Each display area placeholder thus includes structural information about where to invoke additional medical image display protocols, if any. Defining structural relationships in the display protocol may enable further automated capabilities in medical image interpretation workflows. For example, structural information of a first medical image display protocol references a second medical image display protocol in a first display area placeholder. Different medical images may be displayed according to the first medical image display protocol, and inherently, the second medical image display protocol, when a different user request selecting different medical images is received. Further examples of layouts defined by medical image display protocols are described with respect to FIGS. 3-8.

Turning to FIG. 3, graphical representations of a first medical image display protocol, a second medical image display protocol, and a display which is the result of invoking the first medical image display protocol, and inherently the second medical image display protocol, are shown. FIG. 3 is described with respect to the method 200 of FIG. 2. A first medical image display protocol 302 defines a first layout 304 including a first display area placeholder 306, a second display area placeholder 308, a third display area placeholder 310, and a fourth display area placeholder 312. The first display area placeholder 306 references a second medical image display protocol 322. The second display area placeholder 308 defines a first viewport placeholder "B", the third display area placeholder 310 defines a second viewport placeholder "C", and the fourth display area placeholder 312 defines a third viewport placeholder "D".

The first display area placeholder 306 is positioned in a top left corner of the display and the viewport placeholder "B" is positioned in a top right corner of the display, such that a right side of the first display area placeholder 306 is in contact with a left side of the viewport placeholder "B". Viewport placeholder "C" is positioned in a bottom left corner of the display and the viewport placeholder "D" is positioned in a bottom right corner of the display, such that a top of "C" is in contact with a bottom of the first display area placeholder 306, a top of "D" is in contact with a bottom of "B", and a right side of "C" is in contact with a left side of "D". A structural relationship of viewport placeholders and the display area placeholder of the first layout 304 is defined by the first medical image display protocol 302, where the structural relationship includes a position of each of the display area placeholders, including viewport placeholders, on the display and with respect to each other. For example, the first medical image display protocol 302 may define the first display area placeholder 306, which refers to the second medical image display protocol 322, as being to the left of "B" and/or above "C". The structural relationship among viewport placeholders may be defined based on characteristics of an image used to populate the viewport placeholder. For example, viewport placeholder "A" may be a sagittal view, "B" may be a first axial view, "C" may be a coronal view, and "D" may be a second view. In some examples, the structural relationship may be user-defined. In other examples, the structural relationship may be defined using AI and/or machine learning to identify commonly used structural relationships in other display protocols.

The second medical image display protocol 322 defines a second layout 324 including a fifth display area placeholder 326, a sixth display area placeholder 328, and a seventh display area placeholder 330. The fifth display area placeholder 326 defines a fourth viewport placeholder "E", the sixth display area placeholder 328 defines a fifth viewport placeholder "F", and the seventh display area placeholder 330 defines a sixth viewport placeholder "G". The second medical image display protocol 322 defines a structural relationship among the display area placeholders included in the second layout 324.

When the first medical image display protocol 302 is invoked, the second medical image display protocol 322 is inherently invoked. The first display area placeholder 306 of the first layout 304 references the second medical image display protocol 322. Invoking the first medical image display protocol results in generation of a viewing layout 344 for display on the display device. The viewing layout 344 is composed of the first layout 304 with the second layout 324 positioned in the first display area placeholder 306.

Figure 4:
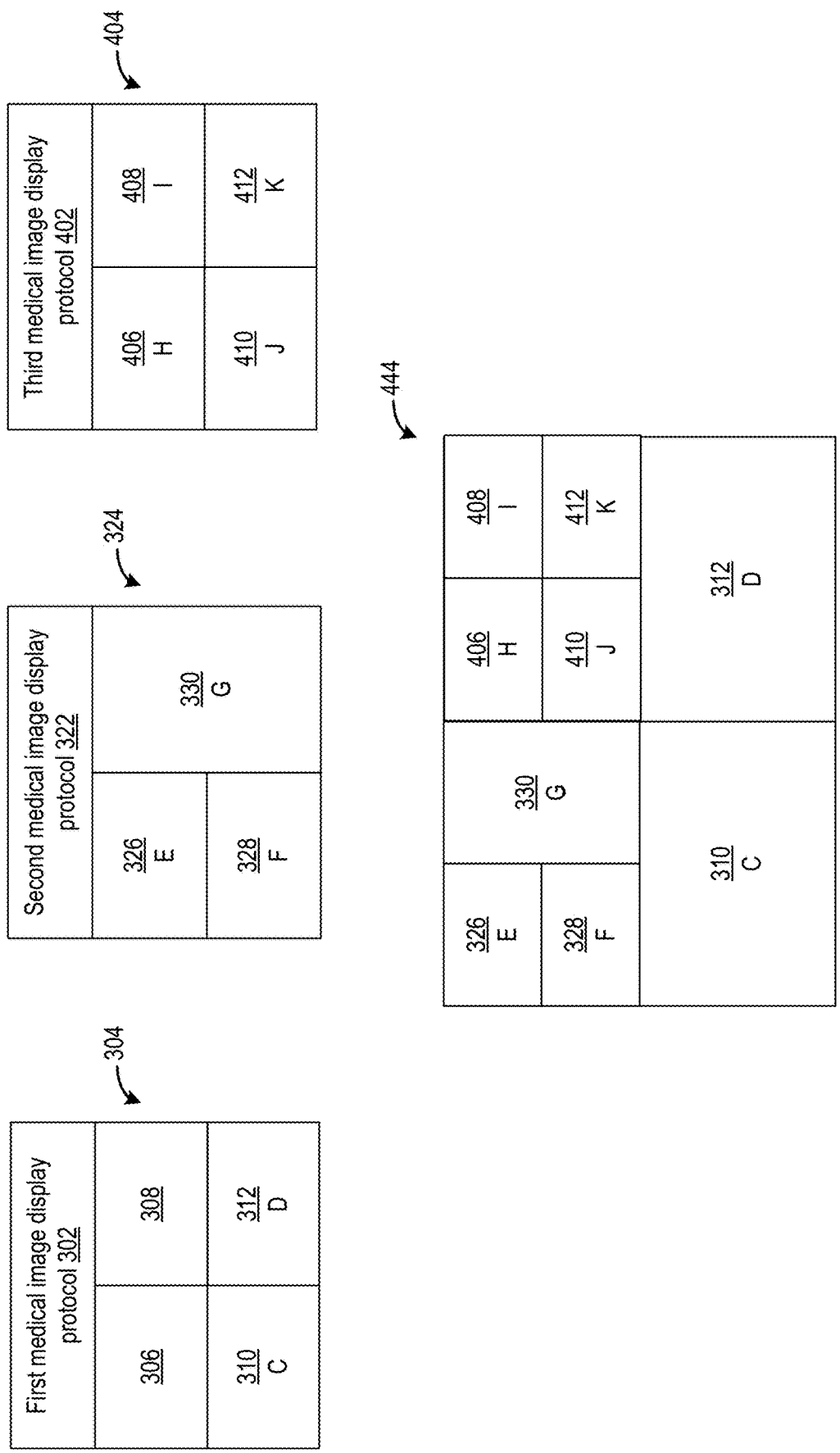
FIG. 4 shows a first example graphical representation of a first medical image display protocol which references a second medical image display protocol and a third medical image display protocol.

The structural relationship in the first layout 304, among a display area placeholder which references the second medical image display protocol and display area placeholders which reference viewport placeholders, may be defined based on characteristics of an image used to populate the viewport placeholder and characteristics of images used to populate viewport placeholders of the second medical image display protocol. In some examples, more than one display area placeholder of a medical image display protocol may reference another medical image display protocol. FIG. 4 shows a second example graphical representation, where the first medical image display protocol 302 may include the first display area placeholder 306 and the second display area placeholder 308, which each refer to additional medical image display protocols. The second medical image display protocol 322 is as described with respect to FIG. 3. A third medical image display protocol 402 defines a third layout 404 including an eighth display area placeholder 406, a ninth display area placeholder 408, a tenth display area placeholder 410, and an eleventh display area placeholder 412. The eighth display area placeholder 406 defines a seventh viewport placeholder "H", the ninth display area placeholder 408 defines an eighth viewport placeholder "I", the tenth display area placeholder 410 defines a ninth viewport placeholder "J", and the eleventh display area placeholder 412 defines a tenth viewport placeholder "K". In this way, invoking the first medical image display protocol 302 inherently invokes the second medical image display protocol 322 and to the third medical image display protocol 402. A viewing layout 444 is generated, and includes medical images which correspond to the respective medical image characteristic parameter s of viewport placeholders of each of the first medical image display protocol 302, the second medical image display protocol 322, and the third medical image display protocol 402. In this way, invoking the first medical image display protocol 302 divides the display area into sections (e.g., the plurality of display area placeholders of the first layout 304) and divides sections of the first layout 304 into subsections (e.g., the plurality of display area placeholders of the second layout 324 and of the third layout 404). The iterative, recursive behavior of the display protocols described herein is further shown in an example where the second medical image display protocol references the third medical image display protocol, as described with respect to FIG. 5.

Figure 5:
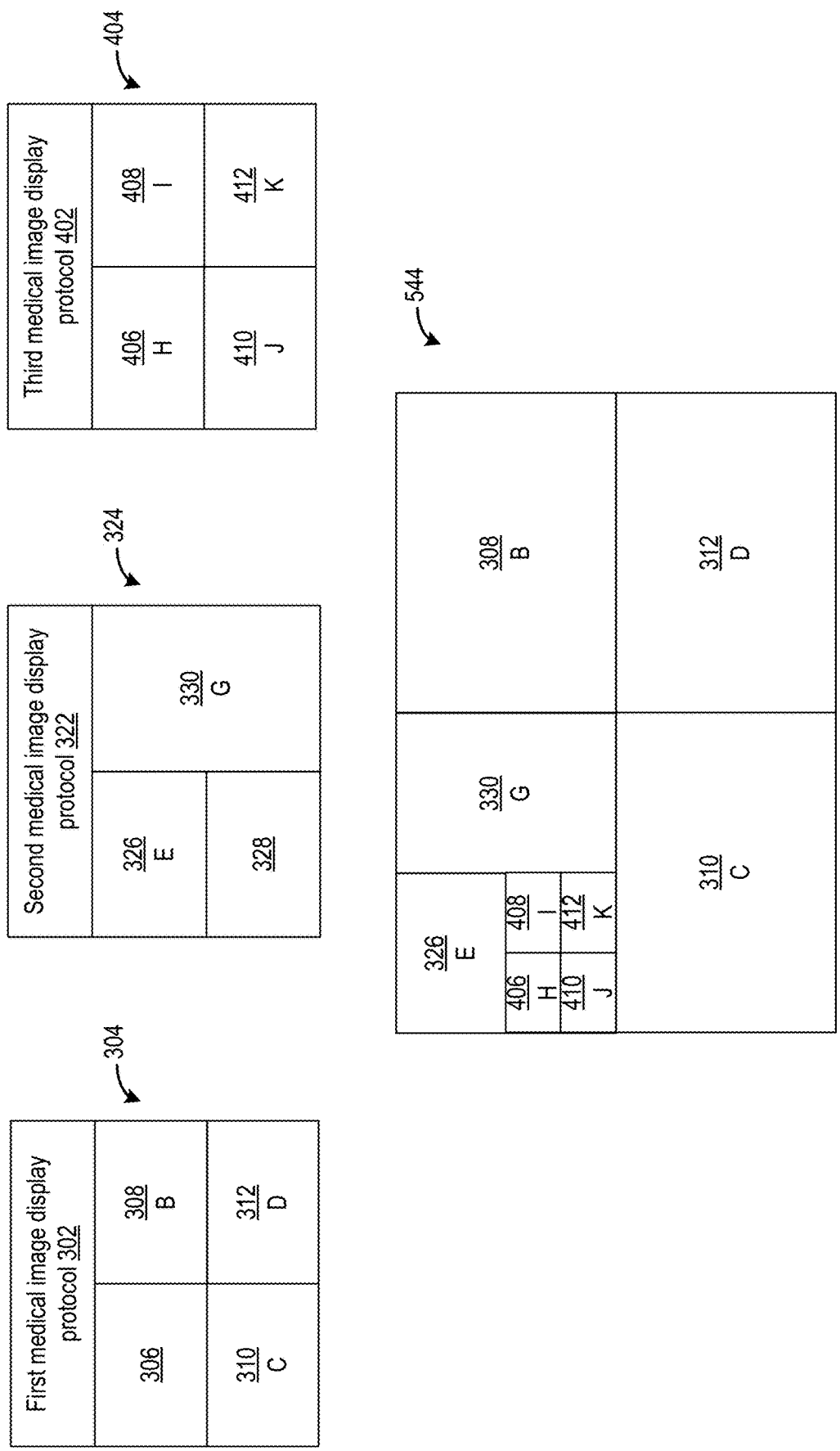
FIG. 5 shows a second example graphical representation of a first medical image display protocol which references a second medical image display protocol and a third medical image display protocol.

FIG. 5 shows a third example graphical representation, where the first medical image display protocol 302 may include the first display area placeholder 306 which refers to the second medical image display protocol 322, and where the second medical image display protocol 322 further includes the sixth display area placeholder 328 which refers to the third medical image display protocol 402. The first medical image display protocol 302, the second medical image display protocol 322, and the third medical image display protocol 402 are otherwise configured as described with respect to FIGS. 3-4. In this way, invoking the first medical image display protocol 302 inherently invokes the second medical image display protocol 322 and the third medical image display protocol 402. A viewing layout 544 is generated, and includes medical images which correspond to the medical image characteristic parameters of viewport placeholders of each of the first medical image display protocol 302, the second medical image display protocol 322, and the third medical image display protocol 402. In this way, invoking the first medical image display protocol 302 divides the display area into sections (e.g., the plurality of display area placeholders of the first layout 304), divides sections of the first layout 304 into subsections (e.g., the plurality of display area placeholders of the second layout 324 and of the third layout 404), and divides subsections of the second layout 324 into sub-subsections of the third layout 404.

In some examples, more than one display area placeholder of the first medical image display protocol 302 may reference additional medical image display protocol (e.g., as described with respect to FIG. 4) and an additional medical image display protocol referenced by the first medical image display protocol may itself reference another medical image display protocol. FIG. 6 shows a fourth example graphical representation, where the first medical image display protocol 302 may include the first display area placeholder 306 which refers to the second medical image display protocol 322, and where the second medical image display protocol 322 further includes the sixth display area placeholder 328 which refers to the third medical image display protocol 402. The first medical image display protocol 302 further includes the second display area placeholder 308 which may refer to a fourth medical image display protocol 602. A fourth layout 604 defined by the fourth medical image display protocol 602 includes a twelfth display area placeholder 606, which defines an eleventh viewport placeholder "L", and a thirteenth display area placeholder 608, which defines a twelfth viewport placeholder "M". The first medical image display protocol 302, the second medical image display protocol 322, and the third medical image display protocol 402 are otherwise configured as described with respect to FIGS. 3-4. In this way, invoking the first medical image display protocol 302 inherently invokes the second medical image display protocol 322, the third medical image display protocol 402, and the fourth medical image display protocol 602. A viewing layout 644 is generated, and includes medical images which correspond to the medical image characteristic parameter s of viewport placeholders of each of the first medical image display protocol 302, the second medical image display protocol 322, and the third medical image display protocol 402. In this way, invoking the first medical image display protocol 302 divides the display area into sections (e.g., the plurality of display area placeholders of the first layout 304), divides sections of the first layout 304 into subsections (e.g., the plurality of display area placeholders of the second layout 324, and divides subsections of the second layout 324 into sub-subsections of the third layout 404.

FIGS. 3-6 show examples arrangements of layouts defined by medical image display protocols. FIG. 7 shows a plurality of example medical image display protocols 700 which may be stored in the display protocol library 118 of FIG. 1 and used in the method 200. The example medical image display protocols of FIG. 7 may include at least one medical image display protocol which may be used as the first medical image display protocol, where the first medical image display protocol is recursively built using additional medical image display protocols to which the first medical image display protocol refers when invoked. Some, but not all, of the medical image display protocols of FIG. 7 may be used as the first medical image display protocol. For example, some of the medical image display protocols may be referred to by another invoked medical image display protocol, but may not itself refer to other medical image display protocols. Described another way, at least some of the example medical image display protocols of FIG. 7 may be applied standalone and be used as building blocks to define more complex display protocols (e.g., which refer to more than one display protocol).

A first example medical image display protocol defines a first example layout 702, which includes a first display area placeholder defining a viewport placeholder "Ser 1", a second display area placeholder defining a viewport placeholder "Ser 2", and a third display area placeholder, which references a "MPR Ser 3" medical image display protocol. A second example medical image display protocol defines a MPR layout 704, and includes four equally sized and shaped display area placeholders which each define a viewport placeholder. The second example medical image display protocol may be labeled as a MPR display protocol in the display protocol library 118, in some examples. Each of the viewport placeholders of the MPR display protocol defines the medical image characteristic parameter of the group of medical images s for one of a sagittal medical image, a coronal medical image, an axial medical image, and a VV medical image. In some examples, the third display area placeholder of the first example medical image display protocol refers to the MPR display protocol, such that when the first example medical image display protocol is invoked, the MPR display protocol is also invoked. A resulting layout, not shown in FIG. 7, includes the viewport placeholders defined in the MPR layout 704 sized to fit in the third display area placeholder while retaining a size relative to each other (e.g., each of the four display area placeholders are equally sized and shaped).

Additional example display protocols as described herein may be referenced by and included in another medical image display protocol. For example, the following example display protocols may be implemented as the second medical image display protocol, the third medical image display protocol, and/or the fourth medical image display protocol, as described with respect to FIGS. 2-6. A third example medical image display protocol defines a third example layout 706, which includes a first display area placeholder defining a viewport placeholder "Seq 1", a second display area placeholder defining a viewport placeholder "Seq 2", and a third display area placeholder defining a viewport placeholder which includes the same the medical image characteristic parameter s as the viewport placeholder "Seq 1" and displays the corresponding medical image subtracted with its mask. The third example medical image display protocol thus generates the layout 704 which includes an image group containing multiple subtraction sequences. "Seq 1" and "Seq 2" display sequences, and the third display area placeholder displays a subtracted sequence. In the example described herein, the third display area placeholder defaults to displaying the first subtracted sequence (e.g., "Seq 1"), however in other examples, other sequences may be displayed.

A fourth example medical image display protocol defines a fourth example layout 708, which includes a first display area placeholder referencing a viewport placeholder for an image group with a lung window, and a second display area placeholder referencing a viewport placeholder for an image group with a bone window. The fourth example medical image display protocol matches to one image group, where the same image group is displayed in two viewports for comparison (e.g., with different window/level settings).

A fifth example medical image display protocol defines a fifth example layout 710, including a single display area placeholder defining a single viewport placeholder, where the viewport placeholder includes the medical image characteristic parameter for at least one image to be displayed with CAD findings as overlaid markings. For example, the display protocol matches to one SR instance and an image group of all images referenced therein. Images are displayed as a stack with CAD findings overlaid on the images.

A sixth example medical image display protocol defines a sixth example layout 712, which divides a display area into two equally sized and shaped, horizontally aligned display area placeholders. A first display area placeholder on a left side of the display area includes a medical image characteristic parameter for a left breast, and a second display area placeholder on a right side of the display area includes parameter medical image characteristic parameter for a right breast. In this way, the left breast and the right breast of a patient may be displayed in opposite directions with an aligned chest line. This may assist in mammography displays.

As described with respect to FIGS. 2-7, display area placeholders may define a viewport placeholder which includes parameter medical image characteristic parameter indicating a desired medical image type to be positioned in the viewport placeholder, where the medical image has a corresponding characteristic. FIG. 8 shows a comparison of generating a display using a conventional display protocol versus using the medical image display protocol described herein (e.g., with respect to FIG. 2), where a first medical image display protocol is a recursive model which includes at least one additional medical image display protocol.

In a conventional medical image display protocol, a layout 802 is defined as a collection of viewports, and data sets are assigned to each viewport. For example, the layout 802 shows a CT study displayed according to a first display protocol. The first display protocol defines ten viewport placeholders (VP): a scout image in VP1, series 1 in VP2, a coronal view of series 2 in VP3, a sagittal view of series 2 in VP4, a first axial view of series 2 in VP5, a second axial view of series 2 in VP6 (e.g., which may be the same as or different from the first axial view of series 2), a coronal view of series 3 in VP7, a sagittal view of series 3 in VP8, a first axial view of series 3 in VP9, and a second axial view of series 3 in VP10 (e.g., which may be the same as or different from the first axial view of series 3). Invoking the conventional medical image display protocol includes dividing a display area of a display device into the layout 802 and populating each viewport with a corresponding image based on the assigned dataset. Retrieving each image and populating each viewport individually in a stepwise manner may use a high processing power of the processor and may take an undesirably long amount of time, compared to the method described herein for displaying medical images.

A first medical image display protocol, as described with respect to FIG. 2, may be invoked to divide a display area into a first layout 804 defined by the first medical image display protocol. The first layout 804 includes four equally sized and shaped display area placeholders. Two display area placeholders on a left side of the layout 804 each reference a viewport placeholder, and two display area placeholders on a right side of the layout 804 each reference another display protocol, as further described herein. For example, the first medical image display protocol defines a scout image in VP1, series 1 in VP2, and a display area placeholder (DA) in each of DA3 and DA4. Invoking the first medical image display protocol further includes invoking at least one additional medical image display protocol (e.g., the second medical image display protocol) which is referenced by a display area placeholder of the first layout (e.g., DA3 and DA4). Using a recursive model, more than one display protocol can be defined. For example, the first medical image display protocol may refer to a second medical image display protocol, such as the MPR display protocol as described with respect to FIG. 7. Briefly, the MPR display protocol defines a second layout 806 with four viewports: a coronal view in VP1, a sagittal view in VP2, a first axial view in VP3, and a fourth axial view in VP4. Multiple MPR display protocols may be included to assist in volume rendering, maximum intensity projection, oblique views, and so on. For example, DA3 and DA4 of the first medical image display protocol may each refer to the MPR display protocol for different image sets. Invoking the first medical image display protocol includes invoking the MPR display protocol for series 2 in DA3 and invoking the MPR display protocol for series 3 in DA4.

Generating a display according to the methods described herein may reduce processing power and time spent generating the display, compared to conventional methods. For example, with respect to FIG. 8, instead of manually defining a layout of medical images for DA3 and DA4, defined MPR display protocols are invoked to automatically organize and populate the viewport placeholders. As medical image display protocols are stored on the display protocol library, they may be accessed by different users at the same or different institutions. This may assist in implementing the same display protocols both in and among institutions. Additionally, structural information of a present medical image display protocol may prevent unintended user interactions with the display, such as removing a viewport or dragging and dropping another image group into a viewport of the MPR display protocol if the current viewing context is still the MPR view. As there may not be hardcoded rules in the structural information, the MPR display protocol may be changed to another medical image display protocol to achieve the desired image layout.

As described above, the medical image display protocols described herein define both what resources are used to populate display area placeholders (e.g., medical images for viewport placeholders or other medical image display protocols) and structural relationships among display area placeholders. For example, structural relationships among the display area placeholders of a medical image display protocol may be understood and applied by software to enable further automated capabilities in medical image interpretation workflows. An example of using structural relationship information to populate viewport placeholders with different medical images is described with respect to FIG. 9, and an example of using structural relationship information to reposition viewport placeholders in a display area is described with respect to FIG. 10.

FIG. 9 illustrates a method 900 for automatically populating viewport placeholders with a second set of images which replace a first set of images initially used to populate the viewport placeholders. For example, a user request received by a processor (e.g., the processor 130 of FIG. 1) may include a selection of a first set of medical images and a first medical image display protocol. The method 200 of FIG. 2 may be executed, which includes retrieving and invoking the first medical image display protocol and any other medical image display protocols referenced thereby, as well as retrieving medical images from the first set of medical images and populating viewport placeholders with medical images which correspond with medical image characteristic parameters s of the viewport placeholders. In some examples, it may be desirable to use a different medical image to populate a viewport placeholder than what has automatically populated the viewport placeholder. For example, a first medical image may be blurry or not capture the full region of interest. It may then be desirable to replace the first medical image with a second medical image which shows the region of interest with increased clarity.

At 902, the method 900 includes receiving a first image replacement request. The first image replacement request may include at least one of: deletion of the first image from the first set of medical images, deletion of the first image from the viewport placeholder, and/or dragging and dropping a second medical image into the viewport placeholder populated by the first medical image, for example.

At 904, the method 900 includes determining if characteristics of the second medical image correspond with the medical image characteristic parameter s of the viewport placeholder. If it is determined that characteristics of the second medical image do not correspond with the medical image characteristic parameter s of the viewport placeholder, at 906, the first image is not replaced (e.g., the first image populates the viewport placeholder) and the method 900 ends. If it is determined that characteristics of the second medical image correspond with the medical image characteristic parameter of the viewport placeholder, at 908, the first image is replaced by the second image (e.g., the second medical image populates the viewport placeholder).

Turning to FIG. 10, a method 1000 is shown which uses structural relationship information to reposition display area placeholders in a display area. The method 1000 enables automatic rearrangement of images based on requested movement of a first viewport placeholder. For example, it may be desired to have a first viewport placeholder, and therefore, corresponding first medical image, positioned on a right side of a display area. The medical image display protocol which defines positions of the plurality of display area placeholders within the display area also defines structural relationships among the display area placeholders. For example, as described with respect to FIGS. 3-6, a first display area placeholder may be positioned above a third display area placeholder and to the right of a second display area placeholder.

At 1002, the method 1000 includes receiving a first display area placeholder movement request. For example, the first display area placeholder movement request may include dragging and dropping the second display area placeholder into the position of the first display area placeholder. At 1004, the method 1000 includes identifying the structural relationship of the first display area placeholder and other display area placeholders of the first layout. For example, the first display area placeholder movement request may position the first display area placeholder to the left of the second display area placeholder. At 1006, the method 1000 includes repositioning the display area placeholders. For example, this includes moving the first display area placeholder to the requested position. In some examples, as further described with respect to FIG. 11, the third display area placeholder may also be moved to the left of the second display area placeholder, such that the third display area placeholder is positioned below the first display area placeholder.

Turning to FIG. 11, an example graphic representation 1100 of repositioning display area placeholders according to the method 1000 of FIG. 10 is shown. A first layout 1102 may be the layout defined by the first medical image display protocol, and includes a first display area placeholder 1104, a second display area placeholder 1106, and a third display area placeholder 1108. The first display area placeholder 1104 is positioned above the third display area placeholder 1108, such that a bottom edge of the first display area placeholder 1104 is in contact with a top edge of the third display area placeholder 1108. The second display area placeholder 1106 is positioned to the right of the first display area placeholder 1104 and the third display area placeholder 1108, such that a left side of the second display area placeholder 1106 is in contact with a right side of each of the first display area placeholder 1104 and the third display area placeholder 1108.

As described with respect to FIG. 10, a processor may receive a first display area placeholder movement request, which includes a request to move the first display area placeholder 1104 to a right side of the display area, as shown in a second layout 1112. The method 1000 of FIG. 10 further includes identifying structural relationship among the first display area placeholder 1104 and other display area placeholders of the first layout 1102. The structural relationship among the placeholders of the first layout 1102 may be defined by the first medical image display protocol. In some examples, different elements of the structural relationship may have different weights. For example, it may be more desirable to display the first display area placeholder 1104 above the third display area placeholder 1108 than it is to display the first display area placeholder 1104 and the third display area placeholder 1108 on a left side of the display area. The method 1000 may identify relationship elements with a highest weight, and may reposition additional display area placeholders based on the highest weight relationship element. For example, as shown in the second layout 1112, the third display area placeholder 1108 may be relocated to the right side of the display area, such that the third display area placeholder 1108 is positioned below the first display area placeholder 1104. The second display area placeholder 1106 is positioned on the left side of the display.

In some examples, all of the relationship elements may have the same weight. Moving the first display area placeholder 1104 to the right side of the display area may include resizing the first display area placeholder 1104 to fill the size and shape of the second display area placeholder 1106, as shown in the first layout 1102 and a third layout 1122. The second display area placeholder 1106 may be moved to the original position of the first display area placeholder 1104 (e.g., in the first layout 1102). In some examples, the resulting layout may be saved as a new medical image display protocol, and stored in the display protocol library 118 for future use.

Systems and methods area described herein for a display protocol model having a recursive modular structure. A first medical image display protocol may include at least one display area placeholder which refers to a second medical image display protocol, such that when the first medical image display protocol is invoked, the second medical image display protocol is inherently invoked. In some examples, additional display area placeholders of the at least one display area placeholder of the first medical image display protocol may refer to additional medical image display protocols. Additionally, in some examples, the second medical image display protocol may include at least one display area placeholder which refers to additional medical image display protocols. The recursive structure of the first medical image display protocol enables multiple medical image display protocols to be executed by invoking the first medical image display protocol. Compared to conventional display protocols which individually divides and defines sections of a display area, the recursive structure of the display protocol described herein reduces processing demand and reduces time used to generate a layout of medical images for a display area. Additionally, the recursive, modular structure of the medical image display protocol methods described herein enables building and invoking medical image display protocols which have composability. Because a medical image display protocol may include references to other display protocols in at least one display area placeholder (e.g., instead of explicitly containing instructions for that display protocol, or being defined as a viewport placeholder), an infinite number of unique display layouts may be generated from a finite number of medical image display protocols.

The disclosure also provides support for a method for displaying multiple images based on multiple modular display protocols, comprising: receiving, via a graphical user interface (GUI) displayed on a display device, a first user request to view one or more medical images from a set of medical images using a first medical image display protocol, in response to the first user request, retrieving the first medical image display protocol from a display protocol library stored on a memory, the first medical image display protocol including a first layout having a plurality of display area placeholders, wherein each display area placeholder of the plurality of display area placeholders either defines a viewport placeholder having a respective medical image characteristic parameter that defines a characteristic of at least one medical image to be displayed in that viewport placeholder, or references a display protocol stored in the display protocol library, invoking, via a processor, the first medical image display protocol to divide a display area of the display device into the plurality of display area placeholders, determining that a first display area placeholder of the plurality of display area placeholders references a second medical image display protocol, and in response, retrieving the second medical image display protocol from the display protocol library, the second medical image display protocol including a second layout having one or more additional display area placeholders, invoking, via the processor, the second medical image display protocol to divide the first display area placeholder into the one or more additional display area placeholders, and populating each display area placeholder which defines a viewport placeholder with a corresponding medical image from the one or more medical images based on the medical image characteristic parameter for each viewport placeholder and the characteristic of each medical image. In a first example of the method, the method further comprises: determining that a second display area placeholder of the plurality of display area placeholders of the first layout references a third medical image display protocol and, in response, retrieving the third medical image display protocol from the display protocol library, the third medical image display protocol including a third layout having one or more additional display area placeholders, and invoking, via the processor, the third medical image display protocol to divide the second display area placeholder into the third layout. In a second example of the method, optionally including the first example, the method further comprises: determining that a third display area placeholder of the one or more additional display area placeholders of the second layout references a fourth medical image display protocol and, in response, retrieving the fourth medical image display protocol from the display protocol library, the fourth medical image display protocol including a fourth layout having one or more additional display area placeholders, and invoking, via the processor, the fourth medical image display protocol to divide the second display area placeholder into the fourth layout. In a third example of the method, optionally including one or both of the first and second examples, the display protocol library stores a plurality of medical image display protocols, each medical image display protocol including structural information indicating an arrangement and a relative sizing of a plurality of display area placeholders and viewport placeholders of the medical image display protocol. In a fourth example of the method, optionally including one or more or each of the first through third examples, each medical image display protocol stored in the display protocol library includes a class code indicating an application scope and intention of the respective display protocol. In a fifth example of the method, optionally including one or more or each of the first through fourth examples, each medical image display protocol stored in the display protocol library are applied to a data group level. In a sixth example of the method, optionally including one or more or each of the first through fifth examples, the one or more medical images are stored in and retrieved from a medical image database communicably coupled to a client device which includes the GUI and the display device. In a seventh example of the method, optionally including one or more or each of the first through sixth examples, the first user request includes the one or more medical images and associated metadata for each medical image, the metadata including characteristics of the respective medical image, including imaging method used to capture the image (e.g., X-ray, ultrasound, MRI, CT, and so on), an anatomy shown in the image, an image plane (e.g., sagittal, axial, coronal), a type of marking overlaid on the medical image, an alignment of the medical image, and so on. In an eighth example of the method, optionally including one or more or each of the first through seventh examples, the first user request includes an identifier used to locate and retrieve the first medical image display protocol from the display protocol library.

The disclosure also provides support for a system, comprising: a display device having a graphical user interface (GUI), and a processor with instructions stored in a memory that, in response to receiving a user input via the GUI, enable the processor to: recursively generate a viewing layout, which divides a display area of the display device into a first layout having a first plurality of display area placeholders, where a first display area placeholder of the first layout has a medical image or a second layout positioned therein, at least a second display area placeholder, different from the first display area placeholder, has a third layout positioned therein, and a third display area placeholder of the third layout has a medical image or a fourth layout positioned therein, and display the viewing layout via the display device. In a first example of the system, the first display area placeholder is a viewport placeholder which includes medical image characteristic parameters for at least one medical image. In a second example of the system, optionally including the first example, the first display area placeholder references the second layout. In a third example of the system, optionally including one or both of the first and second examples, each layout has at least one display area placeholder. In a fourth example of the system, optionally including one or more or each of the first through third examples, the system is communicably coupled to a display protocol library, and generating the viewing layout includes retrieving at least one medical image display protocol from the display protocol library, the at least one medical image display protocol defining a layout of display area placeholders, and invoking the at least one medical image display protocol via the processor to divide the display area of the display device according to the medical image display protocol. In a fifth example of the system, optionally including one or more or each of the first through fourth examples, the system is communicably coupled to a medical image database having one or more medical images stored thereon, and generating the viewing layout includes retrieving a plurality of medical images selected by a user request, wherein at least one medical image of the plurality of medical images has characteristics which correspond to a medical image characteristic parameter of a viewport placeholder defined by a display area placeholder of the first layout and/or the second layout, and populating each display area placeholder which defines a viewport placeholder with a corresponding medical image from the retrieved one or more medical images based on the medical image characteristic parameter for each viewport placeholder and the characteristic of each retrieved medical image.

The disclosure also provides support for a method for displaying medical images, comprising: recursively generating a viewing layout which divides a display area of a display device into a plurality of medical image viewport placeholders by invoking a first layout having a first plurality of display area placeholders, where at least a first display area placeholder of the first layout is a first viewport placeholder including a first medical image characteristic parameter for at least one medical image, and at least a second display area placeholder, different from the first display area placeholder, includes an identifier of a second layout having a second plurality of display area placeholders positioned therein, wherein invoking the first layout inherently includes using the identifier of the second layout to retrieve the second layout from a display protocol library, and invoking the second layout, where at least a third display area placeholder of the second layout is a second viewport placeholder including a second medical image characteristic parameter for at least one medical image. In a first example of the method, at least a fourth display area placeholder of the first layout includes an identifier of a third layout having a third plurality of display area placeholders, where at least one of the third plurality of display area placeholders is a viewport placeholder including a third medical image characteristic parameter for at least one medical image. In a second example of the method, optionally including the first example, at least a fifth display area placeholder of the third layout has a fourth layout having a fourth plurality of display area placeholders, where at least one of the fourth plurality of display area placeholders is a viewport placeholder including a third medical image characteristic parameter for at least one medical image. In a third example of the method, optionally including one or both of the first and second examples, the method further comprises: retrieving one or more medical images from a medical image database based on a user request, and positioning at least one retrieved medical image in each viewport placeholder, where each of the at least one medical image has a characteristic which corresponds to the medical image characteristic parameter of the respective viewport placeholder, and outputting the viewing layout for display on the display device. In a fourth example of the method, optionally including one or more or each of the first through third examples, the medical image characteristic parameter of a viewport placeholder defines a medical characteristic of at least one medical image to be displayed therein, including a type of imaging method used to capture the image, an anatomy shown in the image, an image plane, a type of marking overlaid on the medical image, and an alignment of the medical image.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for displaying multiple images based on multiple modular display protocols, comprising:

receiving, via a graphical user interface (GUI) displayed on a display device, a first user request to view one or more medical images from a set of medical images using a first medical image display protocol;

in response to the first user request, retrieving the first medical image display protocol from a display protocol library stored on a memory, the first medical image display protocol including a first layout having a plurality of display area placeholders, wherein each display area placeholder of the plurality of display area placeholders either defines a viewport placeholder having a respective medical image characteristic parameter that defines a characteristic of at least one medical image to be displayed in that viewport placeholder, or references a display protocol stored in the display protocol library;

invoking, via a processor, the first medical image display protocol to divide a display area of the display device into the plurality of display area placeholders;

determining that a first display area placeholder of the plurality of display area placeholders references a second medical image display protocol, and in response, retrieving the second medical image display protocol from the display protocol library, the second medical image display protocol including a second layout having one or more additional display area placeholders;

invoking, via the processor, the second medical image display protocol to divide the first display area placeholder into the one or more additional display area placeholders; and populating each display area placeholder which defines a viewport placeholder with a corresponding medical image from the one or more medical images based on the medical image characteristic parameter for each viewport placeholder and the characteristic of each medical image.

2. The method of claim 1, further comprising:

determining that a second display area placeholder of the plurality of display area placeholders of the first layout references a third medical image display protocol and, in response, retrieving the third medical image display protocol from the display protocol library, the third medical image display protocol including a third layout having one or more additional display area placeholders; and invoking, via the processor, the third medical image display protocol to divide the second display area placeholder into the third layout.

3. The method of claim 2, further comprising:

determining that a third display area placeholder of the one or more additional display area placeholders of the second layout references a fourth medical image display protocol and, in response, retrieving the fourth medical image display protocol from the display protocol library, the fourth medical image display protocol including a fourth layout having one or more additional display area placeholders; and invoking, via the processor, the fourth medical image display protocol to divide the second display area placeholder into the fourth layout.

4. The method of claim 1, wherein the display protocol library stores a plurality of medical image display protocols, each medical image display protocol including structural information indicating an arrangement and a relative sizing of a plurality of display area placeholders and viewport placeholders of the medical image display protocol.

5. The method of claim 1, wherein each medical image display protocol stored in the display protocol library includes a class code indicating an application scope and intention of the respective display protocol.

6. The method of claim 1, wherein each medical image display protocol stored in the display protocol library are applied to a data group level.

7. The method of claim 1, wherein the one or more medical images are stored in and retrieved from a medical image database communicably coupled to a client device which includes the GUI and the display device.

8. The method of claim 1, wherein the first user request includes the one or more medical images and associated metadata for each medical image, the metadata including characteristics of the respective medical image, including imaging method used to capture the image, an anatomy shown in the image, an image plane, a type of marking overlaid on the medical image, and/or an alignment of the medical image.

9. The method of claim 1, wherein the first user request includes an identifier used to locate and retrieve the first medical image display protocol from the display protocol library.

10. A system, comprising:

a display device having a graphical user interface (GUI); and a processor with instructions stored in a memory that, in response to receiving a user input via the GUI, enable the processor to:

recursively generate a viewing layout, which divides a display area of the display device into a first layout having a first plurality of display area placeholders, wherein a first display area placeholder of the first layout is a first viewport placeholder which includes medical image characteristic parameters for at least one medical image, at least a second display area placeholder, different from the first display area placeholder, has a second layout positioned therein, and a third display area placeholder of the second layout is a second viewport placeholder or has a third layout positioned therein; and display the viewing layout via the display device.

11. The system of claim 10, wherein each layout has at least one display area placeholder.

12. The system of claim 10, wherein the system is communicably coupled to a display protocol library, and generating the viewing layout includes retrieving at least one medical image display protocol from the display protocol library, the at least one medical image display protocol defining a layout of display area placeholders, and invoking the at least one medical image display protocol via the processor to divide the display area of the display device according to the medical image display protocol.

13. The system of claim 10, wherein the system is communicably coupled to a medical image database having one or more medical images stored thereon, and generating the viewing layout includes retrieving a plurality of medical images selected by a user request, wherein the at least one medical image is part of the plurality of medical images and has characteristics which correspond to the medical image characteristic parameters of the first viewport placeholder, and populating the first viewport placeholder with the at least one medical image.

14. A method for displaying medical images, comprising:

recursively generating a viewing layout which divides a display area of a display device into a plurality of medical image viewport placeholders by invoking a first layout having a first plurality of display area placeholders, where at least a first display area placeholder of the first layout is a first viewport placeholder including a first medical image characteristic parameter for at least one medical image, and at least a second display area placeholder, different from the first display area placeholder, includes an identifier of a second layout having a second plurality of display area placeholders positioned therein, wherein invoking the first layout inherently includes using the identifier of the second layout to retrieve the second layout from a display protocol library, and invoking the second layout, where at least a third display area placeholder of the second layout is a second viewport placeholder including a second medical image characteristic parameter for at least one medical image.

15. The method of claim 14, wherein at least a fourth display area placeholder of the first layout includes an identifier of a third layout having a third plurality of display area placeholders, where at least one of the third plurality of display area placeholders is a viewport placeholder including a third medical image characteristic parameter for at least one medical image.

16. The method of claim 15, wherein at least a fifth display area placeholder of the third layout has a fourth layout having a fourth plurality of display area placeholders, where at least one of the fourth plurality of display area placeholders is a viewport placeholder including a third medical image characteristic parameter for at least one medical image.

17. The method of claim 14, further comprising:
retrieving one or more medical images from a medical image database based on a user request; and
positioning at least one retrieved medical image in each viewport placeholder, where each of the at least one medical image has a characteristic which corresponds to the medical image characteristic parameter of the respective viewport placeholder; and
outputting the viewing layout for display on the display device.

18. The method of claim 14, wherein the medical image characteristic parameter of a viewport placeholder defines a medical characteristic of at least one medical image to be displayed therein, including a type of imaging method used to capture the image, an anatomy shown in the image, an image plane, a type of marking overlaid on the medical image, and an alignment of the medical image.

* * * * *